(12) United States Patent
Kim et al.

(10) Patent No.: US 8,101,411 B2
(45) Date of Patent: Jan. 24, 2012

(54) METHOD FOR PRODUCTION OF COROSOLIC ACID IN SUSPENSION CULTURE OF PLANT CELLS

(75) Inventors: Chang-Heon Kim, Daejeon (KR); Jin-Ah Kim, Jeongeup (KR); Jai-Young Song, Daejeon (KR); Ho-Joon Choi, Daejeon (KR)

(73) Assignee: Samyang Genex Corporation, Seoul (KR)

( * ) Notice: Subject to any disclaimer, the term of this patent is extended or adjusted under 35 U.S.C. 154(b) by 1050 days.

(21) Appl. No.: 11/993,316

(22) PCT Filed: Jun. 30, 2006

(86) PCT No.: PCT/KR2006/002574
§ 371 (c)(1),
(2), (4) Date: Dec. 20, 2007

(87) PCT Pub. No.: WO2007/004827
PCT Pub. Date: Jan. 11, 2007

(65) Prior Publication Data
US 2010/0159545 A1    Jun. 24, 2010

(30) Foreign Application Priority Data
Jun. 30, 2005   (KR) .................. 10-2005-0058377

(51) Int. Cl.
*C12N 5/00*    (2006.01)
*C12N 5/02*    (2006.01)

(52) U.S. Cl. ....................................... 435/420; 435/419

(58) Field of Classification Search ................. 435/373, 435/127, 419, 420
See application file for complete search history.

(56) References Cited

U.S. PATENT DOCUMENTS

| | | | |
|---|---|---|---|
| 6,908,632 B1 | 6/2005 | Zhao et al. | |
| 2005/0020681 A1 | 1/2005 | Takayama et al. | |
| 2005/0255569 A1* | 11/2005 | Matsuyama et al. | 435/127 |

FOREIGN PATENT DOCUMENTS

| | | |
|---|---|---|
| EP | 1022022 | 7/2000 |
| KR | 10-2004-0081733 | 9/2004 |
| WO | WO-03/018043 | 3/2003 |
| WO | WO-2005/012507 | 2/2005 |
| WO | WO-2005/063227 A1 | 7/2005 |
| WO | WO-2005/064002 | 7/2005 |

OTHER PUBLICATIONS

Taniguchi et al. Production of bioactive triterpenes by *Eriobotrya japanica* calli. (2002) Phytochemistry; vol. 59; pp. 315-323.*
Encina et al. An easy and reliable method for establishment and maintenance of leaf and root cell cultures of *Arabidopsis thaliana*. (2001) Plant Molecular Biology Reporter; vol. 19; pp. 245-248.*
European Search Report dated Mar. 2, 2009. Application No. 06769139.4-2405/1899455 PCT/KR2006/002574.
European Search Report dated Jun. 22, 2010. Application No. 06 769 139.4-2403.
International Search Report dated Aug. 8, 2006 PCT/KR2006/002574.
Taniguchi et al., Production of Bioactive Triterpenes by *Eriobotrya japonica* calli, Phytochemistry, pp. 315-323., 2002.

* cited by examiner

*Primary Examiner* — Kent L Bell
(74) *Attorney, Agent, or Firm* — Gifford, Krass, Sprinkle, Anderson & Citkowski, P.C.

(57) ABSTRACT

The present invention relates to a method of producing corosolic acid by using plant cells that produce corosolic acid. More particularly, the present invention relates to a method of producing corosolic acid by using plant cell suspension cultures comprising the steps of: inducing a callus from a tissue of a plant producing corosolic acid; preparing a cell line capable of being cultured in liquid culture medium from the induced callus; culturing the cell line in a suspension culture; and isolating corosolic acid from the culture solution. The present invention has advantage of maximizing productivity by utilizing two-stage culture, treatment with inducing agent, and high cell-density culture in the suspension culture of plant cells producing corosolic acid.

17 Claims, 6 Drawing Sheets

METHOD FOR PRODUCTION OF COROSOLIC ACID IN SUSPENSION CULTURE OF PLANT CELLS

CROSS REFERENCE TO RELATED APPLICATION

This application is the U.S. national phase of PCT/KR2006/002574 filed Jun. 30, 2006, which claims priority of Korean Patent Application 10-2005-0058377 filed Jun. 30, 2005.

BACKGROUND OF THE INVENTION (a) Field of the Invention

The present invention relates to a method for production of corosolic acid comprising the steps of suspension culturing plants cells in medium for cell growth, and suspension cell culturing at a high concentration in medium for cell production with adding an inducing agent.

(b) Description of the Related Art

Corosolic acid represented by the following Structural Formula I is a material present in leaves of Banaba which belongs to Lythraceae, and leaves of Loquat and flesh of Hawthorn which belong to Rosaceae. It has been reported that corosolic acid has the activity of promoting a rapid absorption of glucose into cells, similar to that of insulin (Chem Pharm. Bull. 41(12): 2129-2131, 1993). Further, it has also been shown from clinical demonstration that corosolic acid can rawer blood-sugar levels without any side effects and prevent the re-rise of blood-sugar levels (Journal of Ethnopharmacology 87: 115 117, 2003). Due to such activity, corosolic acid has been employed as a sugar control agent and a therapeutic agent against Type 2 diabetes (U.S. Pat. No. 6,485,760), as well as a weight control agent (U.S. Pat. No. 6,784,206).

[Structural Formula I]

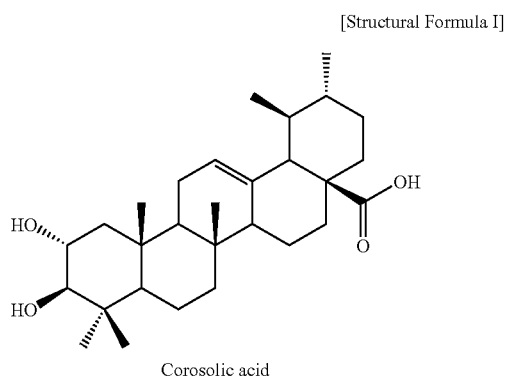

Corosolic acid

At present, corosolic acid is obtained by hot water extraction and alcohol extraction techniques from leaves of Banaba. However, since the amount of corosolic acid naturally present in the leaves is very small, supply of corosolic acid through the direct extraction from natural plants is significantly limited, and thereby, does not meet the increased demand for corosolic acid as raw materials of health foods and medicines. On the other hand, the methods to produce corosolic acid using a semi-synthetic technique from ursolic acid which is a precursor of corosolic acid, has been reported. However, this method also has economic disadvantages because the processes of natural extraction and chemical synthesis should be involved.

Plants serve as sources of many useful secondary metabolites such as alkaloids, steroids, terpenoids and phenol-based compounds which are used in medical materials, dyes, pigments, spices, food additives, etc. Such useful metabolites are currently produced by direct extraction of cultivated plants and purification. However, such conventional processes have the problem of to being greatly affected by geographical and climatic conditions, and policies, as well as change of cultivation environments. Since the content of useful metabolites in plants is not sufficiently high, and most of the plant-originated useful materials produced have complicated structures having been synthesized through various stages of biosynthesis pathways, it is disadvantageous to produce the materials through direct extraction or chemical synthesis methods. Therefore, there has been continuous research to develop methods of mass production of secondary metabolites through plant cell culture techniques.

In spite of a lot of advantages inherent in plant cell culture techniques, low productivity and instability of productivity are considered to be the major hurdles that prevent the techniques from being readily applied to relevant industry. Although it is relatively easy to induce dedifferentiated callus tissues from plant tissues, such induced callus tissues themselves are difficult to apply in relevant industry. Therefore, it is necessary to induce a suspension-culture cell line which can be cultured in liquid culture medium. However, in this regard, it is very difficult to select and establish a superior cell line which can produce secondary metabolites in large amounts and maintain such a high productivity. Further, the steps of selecting and establishing the suspension-cultured cell lines require significant time and effort. Nevertheless, further procedures such as optimizing the medium composition and culturing conditions, selecting and applying, proper elicitors, and developing culturing techniques capable of increasing the productivity, should be required for establishing a mass production system using the selected and established cell lines.

Results of inducing callus tissues from plant bodies of Loquat, and examining the level of production of corosolic acid therefrom have been reported (Taniguchi S. et al., Phytochemistry 59: 315 323, 2002), however the results show that the level of the produced corosolic acid is similar to that in the natural leaves at most. However, there has been neither report nor suggestion regarding the induction and establishment of suspension-cultured cell lines, which is essential for applying the plant cell culture technique to the relevant industry, and a method of mass production of corosolic acid. Likewise for Banaba, there have been no reports regarding the induction and establishment of suspension-cultured cell lines, and a method of mass production of corosolic acid.

SUMMARY OF THE INVENTION

The present invention is to resolve the above problems and satisfy the above requirements. Therefore, the object of the present invention is to provide a method of mass production of corosolic acid using suspension-culture cells of a plant, comprising the steps of culturing the suspension-cultured cells induced from Loquat (*Eriobotrya japonica*) or Banaba (*Lagerstroemia speciosa*) under optimum conditions, and applying various culture conditions and techniques capable of promoting the production of corosolic acid.

More specifically, the object of the present invention is to provide a method of production of corosolic acid by using the suspension culture of plant cells, comprising the steps of: inducing a callus from a plant tissue producing corosolic acid; preparing a suspension-cultured cell line capable of being cultured in liquid culture medium from the induced callus; culturing the suspension-cultured cell lines in a suspension culture; and isolating corosolic acid from the culture solution obtained from the suspension culture step.

Another object of the present invention is to provide a method of producing corosolic acid according to the above method, further comprising a step of culturing by transferring the cell line to a medium containing an inducing agent, after the suspension culture in step. Another object of the present invention is to provide a culturing method capable of increasing the productivity of corosolic acid in the suspension culture, in the above method of mass producing corosolic acid through suspension culture.

Still other object of the present invention is to provide a method of suspension culture of plant cell lines from Loquat or Banaba, comprising the steps: inducing callus from Loquat or Banaba; preparing suspension-cultured cell lines capable of being cultured in liquid culture medium from the callus; and suspension-culturing the suspension-cultured cell lines.

DETAILED DESCRIPTION OF THE EMBODIMENTS

Figure 1:
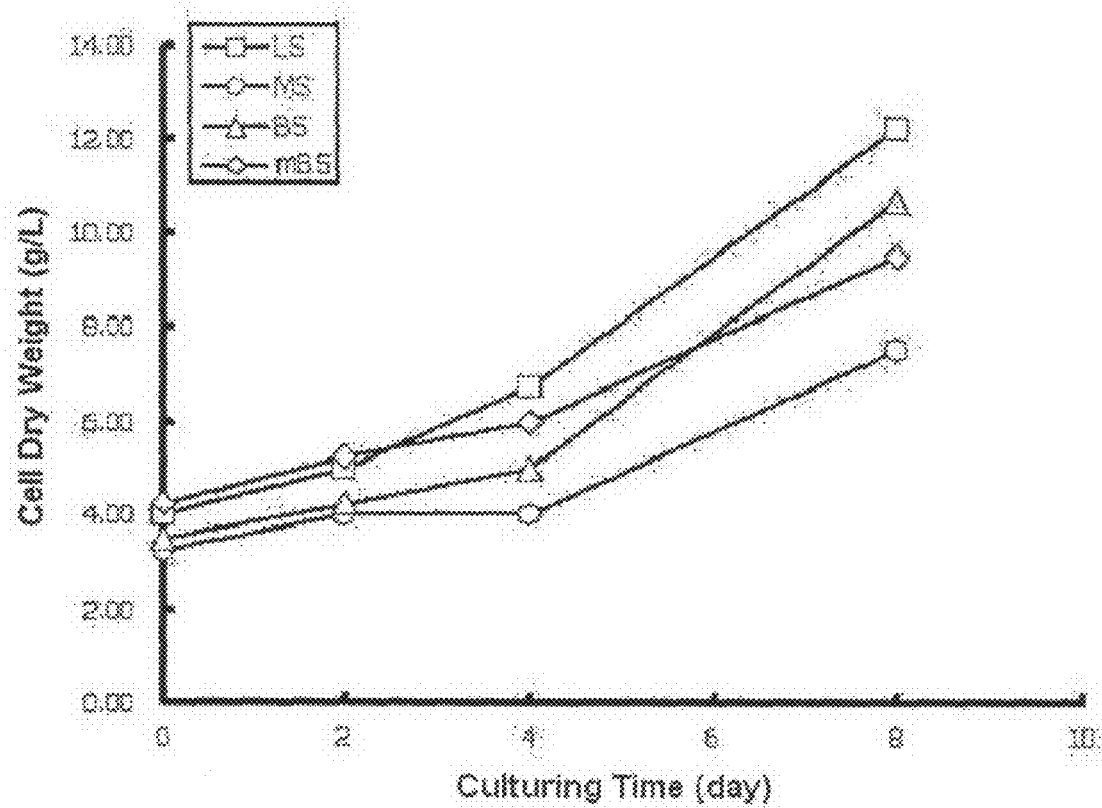
FIG. 1 shows the variation of the cell dry weight during culture of the suspension-cultured cells of Loquat (*Eriobotrya japonica*) obtained in Example 1-2 in four (4) kinds of liquid culture medium.

Hereinafter, the present invention will be described in detail.

The present invention provides a method of mass production of corosolic acid, comprising the steps of inducing callus from plants known to be capable of producing corosolic acid, such as Loquat, Banaba and the like, to establish suspension-cultured cell lines, and culturing the obtained suspension-cultured cell lines in suspension culture.

The above method of mass production of corosolic acid from suspension-cultured cells can be applied to the suspension-cultured cells induced from all plant species which are known to be capable of producing corosolic acid. Said plant capable of producing corosolic acid in the present invention may include Banaba (*Lagerstroemia speciosa*), Loquat (*Eriobotrya japonica*), Ternstroemia (*Ternstroemia gymnanthera*), Hawthorn (*Crataegus pinnatifida*), Tiarella polyphylla and the like, but is not limited thereto. All the tissues of these plants can be induced into callus, which is a dedifferentiated tissue, and then induced into suspension-cultured cell lines.

The induction of callus from the above plants may be performed by treating the plant materials with alcohol and sterilizer to sterilize the surface, transferring explants onto medium containing proper plant growth regulating agents, and culturing them.

The plant tissues capable of being used for the culture of the present invention may include seedings, stems, roots, leaves, flowers, seeds and the like. Young seedings generated by germination from sterilization treated seeds are also used in the present invention. The materials may be effectively sterilized through any conventional sterilizing method such as alcohol immersion, chlorine bleaching treatment, and the like.

Said medium used for induction of the callus may include medium which are commonly used in culturing plant cells, containing nutrients and factors necessary for maintaining the growth ability of the plant cells, such as carbon sources, nitrogen sources, salts, vitamins and the like. Examples of the medium may include Murashige & Skoog medium (hereinafter, 'MS medium'), Gamborg's B5 medium (hereinafter, 'B5 medium'), modified Gamborg's B5 medium (hereinafter, 'mB5 medium'), Linsmaier & Skoog medium (hereinafter, 'LS medium') and the like.

The medium may be used with further addition of various additives, or removal of parts of the components, if necessary. The additives may include proper plant growth regulating agents, such as NAA, BA and the like.

When inducing callus from Loquat, the preferable medium may be LS medium containing 10 μM NAA and 10 μM BA. When inducing callus from Banaba, the preferable medium may be MS medium or LS medium containing 10 μM NAA and 10 μM BA.

The preferable growth temperature for induction of callus may be 20 to 30° C., and preferably, 22 to 27° C.

When the callus reaches full growth, suspension-cultured cell lines can be induced from the callus. The induction of the suspension-cultured cell lines may be performed by transferring the callus into liquid culture medium and carrying out a suspension-culture. The cell culture solution obtained by the suspension culture in the above liquid culture medium for 2 to 3 weeks may be inoculated on medium with the same conditions, to be subject to continuous subculture.

The medium used for the above culture may be either a medium with the same composition as that used for inducing and culturing the callus, except that solidifying components such as agar and the like are removed from the medium used for the callus induction, or a medium with different composition form the medium used for the callus induction, as circumstances require. LS medium may be preferable for the suspension culture of Loquat cells, and B5 medium may be preferable for the suspension culture of Banaba cells. These media may contain additional components to prevent browning and necrosis. Said additional components may include XAD resins, polyvinylpolypyrrolidone (PVPP), active carbon and the like. These additional components added in the medium may serve as an absorbent for phenol-based compounds secreted by the plant cells under stress during induction into suspension-cultured cell lines, in order to promote plant cell growth and contribute to stable induction of the suspension-cultured cell lines. Furthermore, the medium may further comprise antioxidants for preventing oxidation. In the present invention, as a suspension-cultured cell line from Loquat, *Eriobotrya japonica* Lindl. SYG-2 was induced from *Eriobotrya japonica* and deposited at the Korean Collection for Type Cultures located in 52 Eoeun-dong, Yuseong-gu, Daejeon, Korea, on Jun. 22, 2006,with the receipt no. KCTC 10822BP.

Furthermore, as a suspension-cultured cell line from Banaba, *Lagerstroemia speciosa* SYG-3 was induced from *Lagerstroemia speciosa* and deposited at the Korean Collection for Type Cultures located in 52 Eoeun-dong, Yuseong-gu, Daejeon, Korea, on Jun. 22, 2006,with the receipt no. KCTC 10823BP.

The method of the present invention comprises the steps of preparing the suspension-cultured cell line capable of being cultured in liquid culture medium from callus, and culturing the suspension-cultured cell line in a suspension culture.

Generally, in plant cells, the optimum conditions for cell growth and secondary metabolite production differ from each other. Accordingly, in the present invention, the optimization of the medium for plant cell growth in suspension culture and the optimization of the medium for the production of secondary metabolites are separately required.

The medium used for the suspension culture may be any of the commonly used media, and preferably, selected from the group consisting of LS medium, MS medium, B5 medium, mB5 medium, and the like. The suspension culture may be performed at the temperature of 20 to 30° C. for 3 days or longer.

After suspension culturing as above, the method of the present invention may further comprise the step of culturing the suspension-cultured cells in a fresh medium containing elicitors for promoting the production of corosolic acid, if the concentration of carbon source is decreased to 1% (w/v) or lower. In this case, as the medium, any of the commonly used media may be used. Preferably, the medium may be selected from the group consisting of LS medium, MS medium, B5 medium, mB5 medium, and the like. More preferably, the medium may be B5 medium or mB5 medium. In the above two culturing steps, either media with the same composition or media with a different composition may be used.

The culturing time may vary depending on the plant species, and in the present invention, it is possible to perform the culture for 7 days or more.

In the suspension culture of plant cells, proper elicitors may be added for increasing the productivity of secondary metabolites. Such addition of elicitors may be performed at the early stage or the middle stage of culture. Since the biochemical pathways involved in the synthesis of the secondary metabolites vary depending on the kinds of the secondary metabolites, it is necessary to select proper elicitors, and to optimize the processing conditions, in order to increase the productivity of the desired secondary metabolites for large scale production. In the present invention, the elicitors may include biological elicitors and non-biological elicitors. Biological elicitors may be cell-wall extracts or filtrates of fungi, bacteria or yeasts; polysaccharides or glycoproteins derived therefrom; inactivated enzymes; or purification fractions containing purified curdlan, xanthan, chitosan, glucan and the like. Non-biological elicitors may be chemical stimulants or biogenic compounds. The examples of possible elicitors are listed in the following Table 1.

TABLE 1

| Biotic elicitors | Abiotic Elicitors | |
| --- | --- | --- |
| Fungal extracts | Arachidonic acid | Tyramine |
| Bacterial extracts | Elaidic acid | Sodium acetate |
| Yeast extracts | Cyclic AMP | Potassium acetate |
| Chitosan | Dibutyrl Cyclic AMP | Ammonium acetate |
| Lichenan | Methyl jasmone | Mevalonic acid |
| Glucomannan | Cis-jasmone | Farnesyl acetate |
| Pleuran | Miconazol | Geranylgeraniol acetate |
| Glucan | Ferulic acid | Tryptamine |
| Carboxymethylglucan | Vanadyl sulfate | Menthol |
| Sulfoethylglucan | Uniconazol | alpha.-Pinene |
| Hydroxymethylglucan | Paclobutrazol | Trans-cinnamic acid |
| Mannan | Spermine | Cambrene A |
| Xylan | Spermidine | Verticillene |
| Mannobiose | Putrescine | Verticillol |
| Mannotriose | Cadavarine | Camphor |
| Mannopentaose | Protamine sulfate | Quercetin |
| Mannotetraose | Fenpropemorph | Levulinic acid |
| Cellulysin | Prochloraz | Abietic acid |
| Multifect XL | Naptifine | Borneol |
| Multifect CL | EDU | Silver nitrate |
| Resinase | HTA | Norbornadiene |
| Pulpxyme | MPTA | Alar |
| SP431 | Glutathione | 4-amino-5-Hexynoic acid |
| Pectinol | EGTA | Phenylethanolamine |
| Rapidase | AMO-1618 | Phenethylamine |
| Chitinase | Triton X-100 | Glyphosphate |
|  | Benzoic acid | Dihydrocyclo-eucalenol |
|  | Salicylic acid | Methionine sulfoxide |
|  | Propyl gallate | beta.-Hydroxy-phenthylanine |
|  | Sesamol | 5-Methyl-DL-tryptophane |
|  | Chlorocholine chloride | alpha.-Fluorophenylalanine |
|  | 3,4-dichlorophenoxytriethyl-(amine) | 5-2 Aminoethyl-L-cysteine hydrochloride |
|  | Hydroquinone | DCPTA |
|  | Chloroethylphosphonic acid | DIPTA |
|  | Diethyldithiocarbamic acid | ACC |
|  | Nordihydroguairetic acid | Brassinosteroids |
|  | Dithiothreltol | BHA |
|  | Sodium metabisulfite | BHT |
|  | Potassium metabisulfite | OTA |
|  | d-amino-DL-phenylalanine | Chitosan glutamate |
|  | SKF-7997 | Gibberellins |
|  | MER 29 | Abscisic Acid |
|  | Ancymidol | 1,3-Diphenyl urea |
|  | Triadimefon | Diazolidenyl urea |
|  | Phosphon D | Phloroglucinol |
|  | Thiourea | Sodium alginate |
|  | Dextran sulfate |  |
|  | Carragenan |  |

In the present invention, the elicitors may be used at various concentrations depending on the kind of the elicitor used. It is possible to use one or more elicitor together, to improve the effect thereof.

In the present invention, the elicitor for increasing the productivity of corosolic acid is preferably selected from the group consisting of silver nitrate, sodium butyrate, and methyl jasmonate. The added amount of silver nitrate may be 0.01 μM to 500 μM, and preferably, 0.5 μM to 100 μM. The added amount of sodium butyrate may be 0.01 to 500 mM, and preferably, 1 mM to 200 mM. The added amount of methyl jasmonate may be 0.1 μM to 50 mM, and preferably, 1 μM to 10 μM. Furthermore, the elicitors may be added at least once singly or in combination, to increase productivity.

Further, in the suspension culture of plant cells, a high-concentration carbon source may be added to the medium to carry out high-density cell culture and increase the final volumetric productivity of the secondary metabolites. Treatment with a high-concentration carbon source results in an effect obtained by high-osmotic pressure treatment, and provides the cultured cells with available carbon source. Such carbon source may be selected from the group consisting of sucrose, lactose, fructose, glucose and the like. For the high-osmotic pressure treatment, the carbon source may be added to the medium in amount of 1 to 20% (w/v), and preferably 3 to 6% (w/v).

To increase the final volume productivity of the secondary metabolites, the high-density cell inoculation may be conducted, and preferably, 1 to 20 g/L of the cells may be inoculated on the medium and cultured for 7 days or more.

Methods of culturing the plant cells which have been known to those skilled in the art can be applied to an embodiment of the present invention. Examples of the methods include batch culturing, continuous culturing, fed-batch culturing, semi-continuous batch culturing, immobilized culturing, two-phase culturing, and etc. The suitable process can be selected according to the characteristics of the plant cell.

Corosolic acid prepared by the process as described above can be extracted or purified from the solution of plant cell suspension culture by using a known method (U.S. Pat. No. 6,485,760). Corosolic acid can be extracted from the solution of plant cell suspension culture by solvent extraction with hot water, alcohol or organic solvents. In such case, depending on the properties of the solvents, corosolic acid derivatives, and other secondary metabolites as well as corosolic acid can be extracted together at once. Corosolic acid derivatives and other secondary metabolites can be removed by liquid-liquid extraction, re-crystallization, or column chromatography to obtain pure corosolic acid.

Corosolic acid produced according to the method of the present invention can be extracted with methanol, purified with column chromatography purification, and then identified with HPLC.

When plant cells of Eriobotrya japonica is cultured according to the present method, the productivity of corosolic acid is 25 times as high as that of the natural leaf of Eriobotrya japonica, and 18.3 times as high as that of the callus culture of Eriobotrya japonica. In addition, when plant cells of Banaba (Lagerstroemia speciosa) is cultured, the productivity of corosolic acid is 56 times as high as that of the natural leaf.

According to the method of the present invention for culturing plant cells in a suspension culture, which comprises the steps of inducing a callus from Eriobotrya japonica or Lagerstroemia speciosa; preparing a suspension-cultured cell line capable of being cultured in a liquid media; and culturing the suspension-cultured cell line in a suspension culture, plant cells of Eriobotrya japonica and Lagerstroemia speciosa which are the most preferable for mass production of corosolic acid were obtained and deposited at the Korean Collection for Type Cultures (KCTC).

The present invention is further explained in more detail with reference to the following examples. These examples, however, should not be interpreted as limiting the scope of the present invention in any manner.

EXAMPLE 1

Establishment of Suspension Culture of Eriobotrya japonica and Selection of the Optimal Condition for Cell Growth

EXAMPLE 1-1

Callus Induction from Eriobotrya japonica

The leaves and stem were collected from Eriobotrya japonica grown outdoors or in the greenhouse, cut into about 5 cm, surface washed by dishwashing detergent, and rinsed with tap water.

The prepared sample was immersed in 95% ethanol solution for 1 minute, and then sterilized by continuously shaking it in 1% Sodium Hypochlorite solution for 30 minutes, and rinsed three times with sterilized distilled water.

The sterilized sample was cut with a scalpel into slices having 1 cm width×1 cm length, and inoculated on four kinds of medium (LS, MS, B5, and mB5) which were prepared by adding 30 g/L sucrose, 8 g/L agar, 10 μM NAA, 10 μM BA, 1 g/L casein hydrolysate, 1 g/L 2-Morpholinoethanesulfonic acid (MES), and adjusting the pH to 5.7, as indicated in Table 2, and then cultivated in the dark at a temperature of 24° C. for 8 weeks to induce the callus.

The induced callus was transferred to new medium at an interval of 4 weeks. The results of the callus induction and proliferation from Eriobotrya japonica using the four kinds of media are shown in Table 3.

As shown in Table 3, the rates of callus induction in the MS medium and B5 medium were the highest, but callus proliferation in a passage culture on LS medium was fastest.

TABLE 2

| compound(mg/L) | LS | MS | B5 | mB5 |
|---|---|---|---|---|
| $CaCl_2$ | 332.02 | 332.02 | 113.23 | 113.23 |
| $KH_2PO_4$ | 170 | 170 | — | — |
| $NaH_2PO4$ | — | — | 130.44 | 150 |
| $KNO_3$ | 1900 | 1900 | 2500 | 2500 |
| $MgSO_4$ | 180.54 | 180.54 | 121.56 | 246 |
| $NH_4NO_3$ | 1650 | 1650 | — | — |
| $(NH_4)_2SO_4$ | — | — | 134 | 134 |
| $CoCl_2 \cdot 6H_2O$ | 0.025 | 0.025 | 0.025 | 0.025 |
| $CuSO_4 \cdot 5H_2O$ | 0.025 | 0.025 | 0.025 | 0.025 |
| FeNaEDTA | 36.7 | 36.7 | 36.7 | 27.8 |
| $H_3BO_{36.2}$ | 6.2 | 6.2 | 3 | 3 |
| KI | 0.83 | 0.83 | 0.75 | 0.75 |
| $MnSO_4 \cdot H_2O$ | 16.9 | 16.90 | 10 | 10 |
| $Na_2MoO_4 \cdot 2H_2O$ | 0.25 | 0.25 | 0.25 | 0.25 |
| $ZnSO_4 \cdot 7H_2O$ | 8.6 | 8.60 | 2 | 2 |
| myo-Inositol | 100 | 100 | 100 | 10 |
| Nicotinic acid | — | 1 | 1 | 1 |
| Pyridoxine HCl | — | 1 | 1 | 1 |
| Thiamine HCl | 0.4 | 10 | 10 | 10 |
| Riboflavin | — | — | — | 0.015 |

TABLE 3

| Medium | Callus Induction | Callus proliferation |
|---|---|---|
| LS | ++ | +++ |
| MS | +++ | + |
| B5 | +++ | + |
| mB5 | + | + |

EXAMPLE 1-2

Suspension Culture of *Eriobotrya japonica*

The suspension culture was induced by using callus tissue obtained by culturing on the LS medium for 4 weeks according to the method of EXAMPLE 1-1.

Two grams of callus were finely chopped up with a scalpel and added to a 250 ml flask containing 50 ml of 4 kinds of liquid culture medium, and then was cultured by shaking at 110 rpm at 24° C. in the dark.

The suspension culture solution was sampled often and the amount of remaining sugar was measured with the refractometer. As a result, when the remaining sugar decreased to about 1% (w/v), it was transferred to a new passage culture medium.

During the first 2-3 passages cultures, 0.5-1% (w/v) of PVPP, XAD resin or 0.5% (w/v) activated carbon were added to the medium to prevent medium browning and cell oxidation, but were not added in subsequent passage cultures.

Among plant cell lines of *Eriobotrya japonica* obtained from suspension cultures, the plant cell lines with fastest growth rate and the highest production rate were selected and named SYG-2 (*Eriobotrya japonica* Lindl. SYG-2), and then deposited on Jun. 22, 2005 at the Korean Collection for Type Cultures (KCTC) which is located at 1-99 bunji, 52 Eoeundong, Yuseong-gu, Daejeon, Republic of Korea. Accession No. KCTC 10822BP was received.

Sixty mL of cell suspension culture obtained by passage culturing for 2-3 months was inoculated into a 500 mL flask containing 180 ml liquid solution of four kinds of medium and cultured at 150 rpm, and the remaining sugar and cell dry weight were measured every other day.

The cell dry weight was obtained by filtering sampled plant cell culture through Watman no. 4 filter paper using a Buchner funnel, and oven drying at a temperature of 60° C. for 24 hours.

Figure 2:
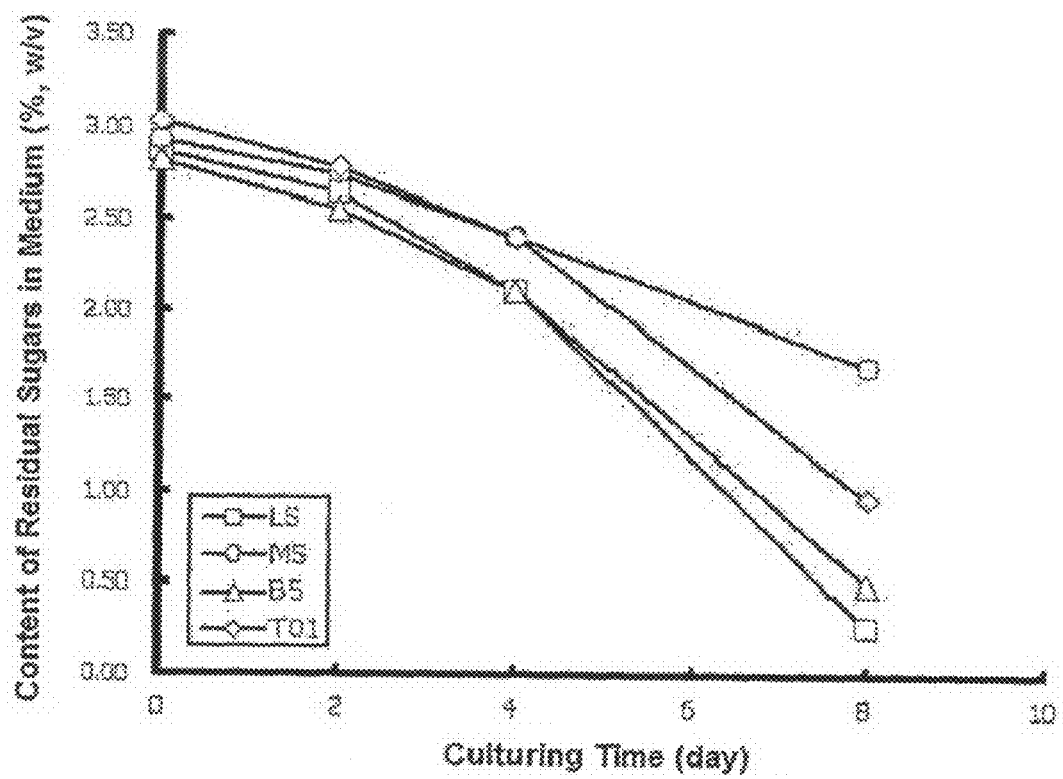
FIG. 2 shows the variation of contents of residual sugars during culture of the suspension-cultured cells of Loquat obtained in Example 1-2 in four (4) kinds of liquid culture medium.

FIG. 1 and FIG. 2 shows the cell dry weight and remaining sugar which were from *Eriobotrya japonica* cell lines suspension cultured on four kinds of medium.

As a result, LS medium was most preferable for fast growth.

In LS medium, the suspension-cultured cell lines of *Eriobotrya japonica* grew to a dry cell weight of 12.2 g/L in only 8 days, which was three times as high as the amount of inoculated cells.

The cell characteristics of *Eriobotrya japonica* obtained by suspension culture are shown in Table 4

TABLE 4

| Culture time(day) | 8 days |
|---|---|
| Maximum dry weight(g/L) | 12.25 |
| Maximum specific growth rate(day$^{-1}$) | 0.202 |

EXAMPLE 1-3

The Treatment of Plant Growth Hormone

The *Eriobotrya japonica* cell lines obtained in EXAMPLE 1-2 were cultured at 24° C. with added NAA and BA as indicated in Table 5 at the beginning of culture, and then the cell dry weight was measured after seven days. The result is shown in FIG. 3.

TABLE 5

| Experiment | NAA concentration | BA concentration |
|---|---|---|
| 1 | 1 μM | 0.1 μM |
| 2 | 5 μM | 0.1 μM |
| 3 | 10 μM | 0.1 μM |
| 4 | 20 μM | 0.1 μM |
| 5 | 1 μM | 1 μM |
| 6 | 5 μM | 1 μM |
| 7 | 10 μM | 1 μM |
| 8 | 20 μM | 1 μM |
| 9 | 1 μM | 10 μM |
| 10 | 5 μM | 10 μM |
| 11 | 10 μM | 10 μM |
| 12 | 20 μM | 10 μM |

Figure 3:
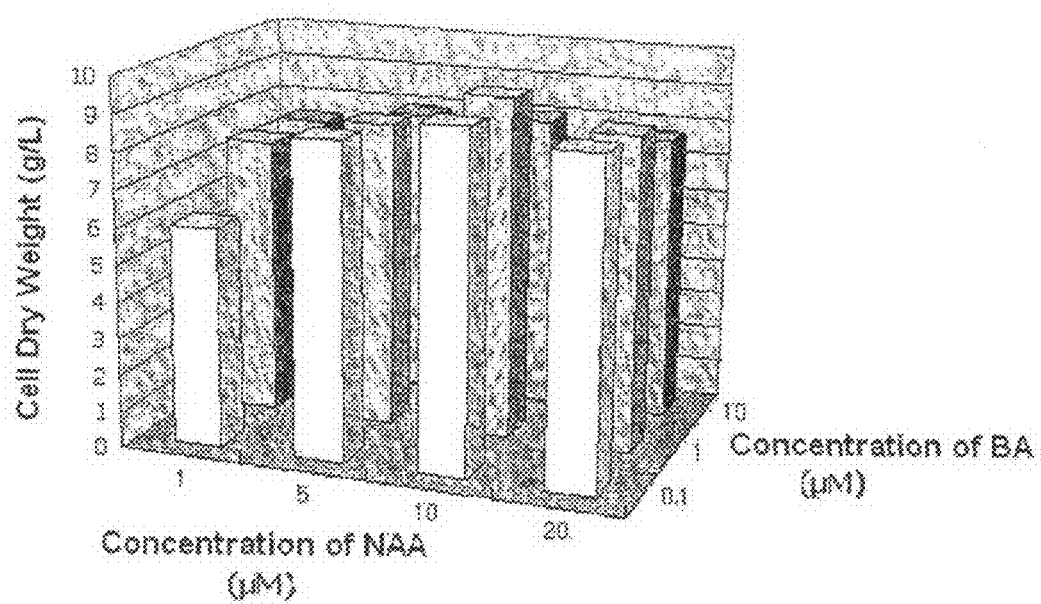
FIG. 3 shows the cell dry weight measured on the $7^{th}$ day of culture, where various concentrations of 6-benzylaminopurine (hereinafter, 'BA') and α-naphtalene acetic add (hereinafter, 'NAA'), which are plant growth regulating agents presented in the following Table 5,are added to the culture medium of suspension-cultured cells of Loquat obtained in Example 1-3.

As shown in FIG. 3, a mixture of 10 μM NAA and 1 μM BA were most preferable for the growth of suspension-cultured cell lines of *Eriobotrya japonica*.

EXAMPLE 2

Suspension Culture of *Eriobotrya japonica*

EXAMPLE 2-1

Suspension Culture of *Eriobotrya japonica*

In the culture solution added by NAA 10 μM and BA 1 μM, suspension-cultured cell lines of *Eriobotrya japonica* were cultured at a temperature of 24° C. for 7 days according to the method of EXAMPLE 1-2.

EXAMPLE 2-2

Separation and Analysis of Corosolic Acid

The cells were collected from suspension culture in EXAMPLE 2-1 after 7 days, and then corosolic acid was separated as follows:

5 ml sample obtained from cell culture solution in EXAMPLE 2-1 were centrifuged to remove the medium solution, sufficiently oven dried at a temperature of 40° C. for 24 hours, and then were ground up using a mortar. Ten mg of the cell powder was initially extracted by shaking for 5 hours or more in 1 ml of ethanol. The initial extract was centrifuged to recover the methanol fraction. The remaining cell powder fraction was extracted a second time by shaking for 1 hour in 1 ml of methanol, and then centrifuged to recover the methanol fraction.

One ml of distilled water was added to 2 ml of the mixture of the initial and secondary extracts to result in a methanol concentration of 60-70%. Then, the solution went through an ODS-column purification process.

Firstly, the ODS column was stabilized with 5 ml of 70% methanol, injected with the sample, and then washed with 5 ml of 70% methanol.

The remaining materials in the column was eluted with 5 ml of 100% methanol, and concentrated in a reduced pressure to prepare the sample to be analyzed.

Corosolic acid was analyzed with HPLC under the following conditions where Chromolith RP 18e (Merck, 100×4.6 mm) column was used and a mixture of 0.05% trifuroacetic acid and 75% methanol as a mobile phase were eluted at a rate of 1 ml/min, and the absorbance at 210 nm were measured. The result is shown in FIG. 4.

Figure 4:
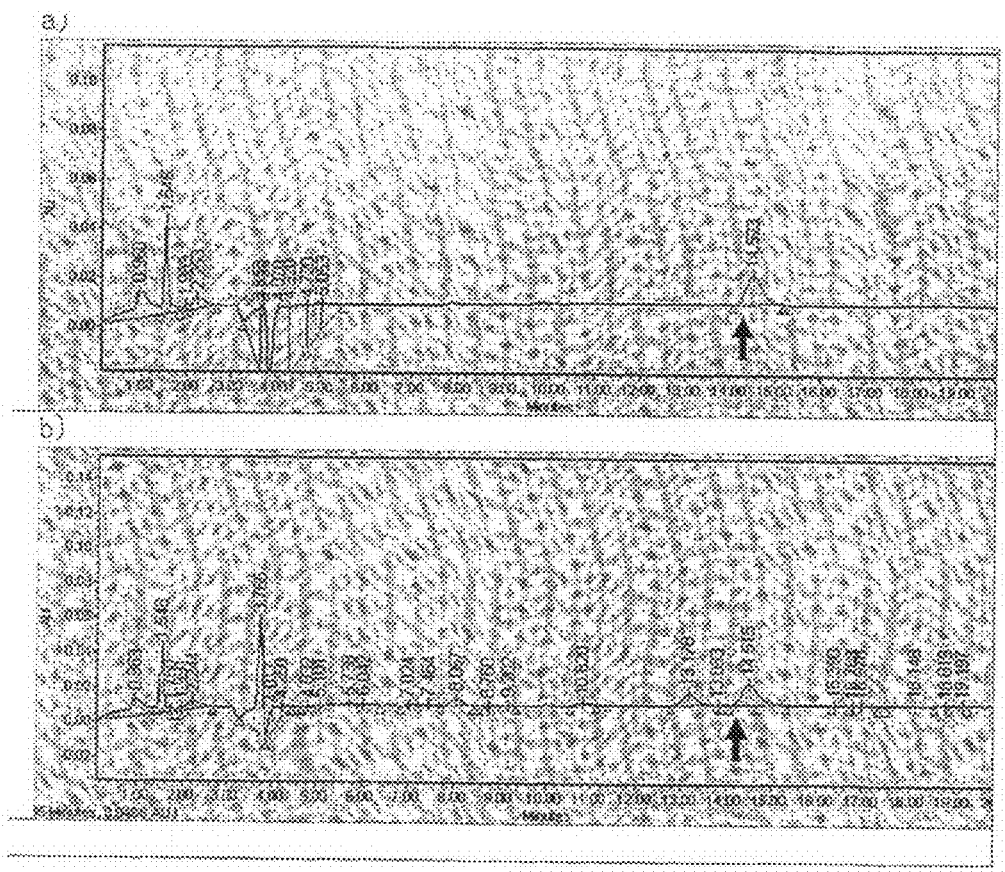
FIG. 4 shows the analysis of High Performance Liquid Chromatography as illustrated in Example 2-2. [(a) corosolic acid standard sample at a concentration of 0.1 mg/ml, (b) methanol extract of the suspension-cultured cells of Loquat]

FIG. 4 shows the analysis of a standard sample of corosolic acid and the suspension-cultured cell line of *Eriobotrya*

*japonica*. a) is 0.1 mg/ml of standard corosolic acid, and b) is a methanol extract of suspension-cultured cell line of *Eriobotrya japonica*.

EXAMPLE 2-3

Selection of Medium for Producing Corosolic Acid

According to Example 1-2, the cell lines obtained in EXAMPLE 2-1 were cultured in four kinds of culture media, collected after 7 days, and then corosolic acid was extracted and the productivity was measured according the method of EXAMPLE 2-1.

The productivity of corosolic acid was quantified by the following method:

The concentration of corosolic acid was calculated from an area of the corosolic acid peak obtained from HPLC analysis by using the standard curve obtained from the peak area of 0.05-1 mg/L standard corosolic acid. The % DW (Dry Weight) was calculated from the calculated concentration of corosolic acid.

% DW content is intended to mean weight % of corosolic acid contained in 1 g of cell dry weight.

The volumetric productivity (mg/L) was calculated by multiplying the calculated % DW content with the cell concentration (g/L, DW) in cell culture.

Figure 5:
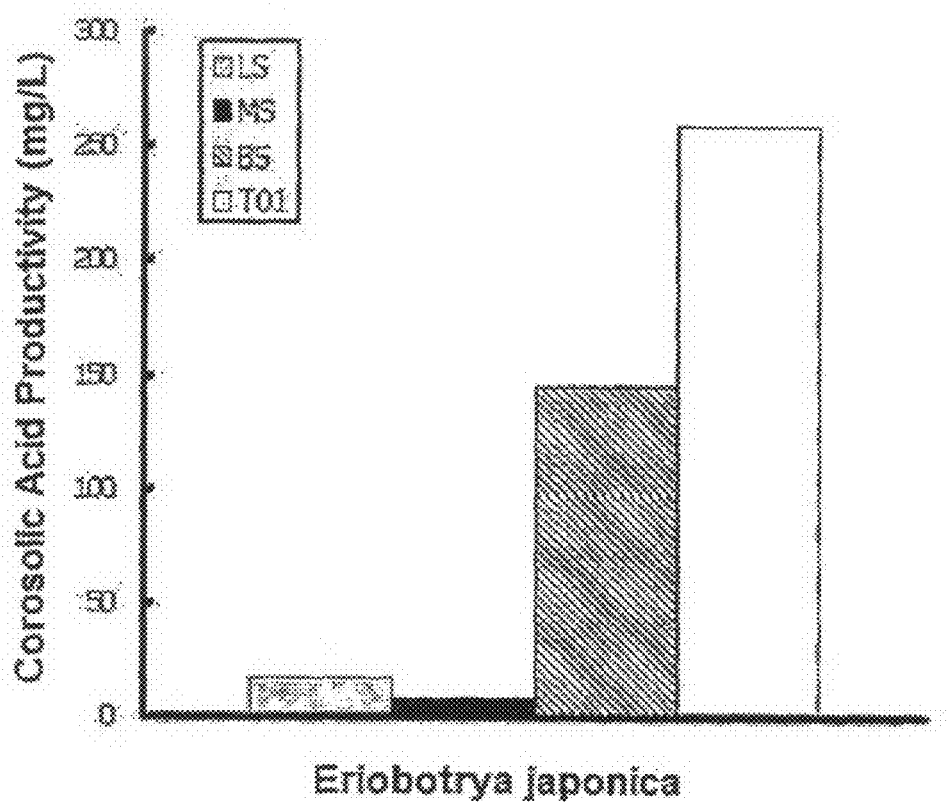
FIG. 5 shows corosolic acid productivity of the cultured cells in Example 2-3.

The productivity obtained from the above method is shown in FIG. 5.

As shown in FIG. 5, the productivity of cell fine of *Eriobotrya japonica* in the suspension culture was largely dependent on the medium. B5 medium and mB5 were preferable for producing corosolic acid, but LS medium and MS medium displayed low productivity of corosolic acid.

In contrast to the result of cell growth in EXAMPLE 1-2, the result showed that the appropriate medium for producing corosolic acid is different from that for cell growth.

EXAMPLE 3

Two-stage Culture 50 ml of the cell lines which were obtained in EXAMPLE 1-2 were cultured in LS medium with addition of 10 μM of NAA and 1 μM of BA, and collected after 7 days, and 50 ml of 2× concentration of mB5 medium were mixed and cultured in a 250 ml flask. According to the method of EXAMPLE 2-3, the productivity of corosolic acid was measured.

TABLE 6

| | Productivity of corosolic acid | |
|---|---|---|
| | (% DW) | (mg/L) |
| Growth stage | 2.69 | 381.77 |
| Production stage | 3.61 | 509.61 |

As shown in Table 6, the suspension-cultured cells of *Eriobotrya japonica* which were inoculated at a ratio of 25% (v/v) in LS medium and cultured for 7 days shows 2.69% DW of the productivity of corosolic acid. The cells which were cultured and then transferred to mB5 medium for 7 days increased by 34.2% to 3.61% DW of the productivity of corosolic acid. This value corresponds to 509.61 mg/L of volumetric productivity.

EXAMPLE 4

Production of Corosolic Acid by High Cell-density Culture

The *Eriobotrya japonica* cells were cultured according to the method of Example 3, except that the concentration of sucrose added to the mB5 medium as the carbon source at the production stage, and the inoculation ratio of *Eriobotrya japonica* cell were varied as in Table 7. According to the method of EXAMPLE 2-3, the cell dry weight and the productivity of corosolic acid were measured.

As shown in Table 7, by high cell-density culture, the suspension-cultured cells of *Eriobotrya japonica* produced a maximum of 23.47 g/L of cell dry weight, and 2604.13 mg/L of volumetric productivity.

TABLE 7

| | | | sucrose concentration | |
|---|---|---|---|---|
| | Culture time | Cell dry weight | Productivity of corosolic acid | |
| Inoculum | (day) | (g/L) | (% DW) | (mg/L) |
| 3%: 3 g/L | 7 | 13.26 | 3.37 | 446.26 |
| 3%: 6 g/L | 7 | 16.83 | 4.86 | 818.46 |
| 6%: 3 g/L | 21 | 22.64 | 11.50 | 2604.13 |
| 6%: 6 g/L | 21 | 23.47 | 10.96 | 2571.51 |

EXAMPLE 5

Production of Corosolic Acid with Addition of Inducing Agent

In the two-stage culture by using high cell-density culture of Example 4, 6% of sucrose was added to mB5 medium at the production stage, and the inoculated amount was 6 g/L cell dry weight. At this time, the cells were cultured for 14 days with the addition of silver nitrate, sodium butylate, and methyl jasmonate at the concentrations shown in Table 8 at the beginning or on the third day, and then the cell dry weight and the productivity of corosolic acid were measured to show the result in Table 8.

TABLE 8

| Treatment Condition | Cell Dry Weight | Productivity of Corosolic acid | |
|---|---|---|---|
| (Addition time) | (g/L) | (% DW) | (mg/L) |
| Control | 25.07 | 4.17 | 1045.37 |
| AgNO3 2 μM (0-day culture) | 26.05 | 4.42 | 1152.07 |
| AgNO3 4 μM (0 day culture) | 25.66 | 6.05 | 1551.78 |
| AgNO3 6 μM (0-day culture) | 24.57 | 5.44 | 1335.86 |
| Sodium butyrate 1.0 mM (3-day culture) | 24.54 | 8.48 | 2081.13 |
| Methyl jasmonate 400 μM ((3-day culture)) | 22.72 | 8.42 | 1913.16 |
| Sodium butyrate 1.0 mM + Methyl jasmonate 400 μM ((3-day culture)) | 22.67 | 9.49 | 2151.38 |

As shown in Table 8, the addition of 2-6 μM of silver nitrate to the culture medium increased the productivity of the suspension-cultured cell. When 4 μM of silver nitrate was added, maximal concentration of cell increased by 45%.

In addition, when 1 mM of sodium butylate and 400 μM of methyl jasmonate were each added, the amount of corosolic acid was increased by 100%. In particular, when 1.0 mM of sodium butylate was added in, combination with 400 μM of methyl jasmonate, the amount of corosolic acid was increased by 128%, and the volumetric productivity was 2151.38 mg/L.

EXAMPLE 6

Production of Corosolic Acid from *Lagerstromia speciosa*

EXAMPLE 6-1

Callus Induction of *Lagerstromia speciosa*

According to the method of EXAMPLE 1-1,leaves and stem were collected from *Lagerstromia speciosa* grown outdoors or in the greenhouse, and callus induction and callus proliferation was performed. The result is shown in Table 9.

As shown in Table 9,the callus induction of *Lagerstromia speciosa* was highest in B5 medium, but in a series of passage cultures, the callus proliferation was fastest in LS medium.

TABLE 9

| Medium | Callus induction | Callus proliferation |
|---|---|---|
| LS | ++ | +++ |
| MS | ++ | ++ |
| B5 | +++ | + |
| mB5 | + | + |

EXAMPLE 6-2

Cell Suspension Culture of *Lagerstroemia speciosa*

Liquid suspension culture was performed according to the method of EXAMPLE 1-2,except that the callus obtained in Example 6-1 was used and that B5 medium was used in the second stage.

The cell characteristics of the *Lagerstromia speciosa* cell culture are summarized in Table 10.

TABLE 10

| Culture time(day) | 14 days |
|---|---|
| Maximum cell dry weight (g/L) | 6.5 |
| Maximum specific growth rate(day$^{-1}$) | 0.089 |

Among plant cell lines of *Lagerstromia speciosa* obtained from suspension cultures, the plant cell lines with the fastest growth rate and highest production rate were selected and named SYG-3 (*Lagerstroemia speciosa* SYG-3), and then deposited on Jun. 22, 2005 at the Korean Collection for Type Cultures (KCTC) located at 1-99 bunji, 52 Eoeun-dong, Yuseong-gu, Daejeon, Republic of Korea. Accession No. KCTC 10823BP was received.

EXAMPLE 6-3

Production of Corosolic Acid with the Suspension-cultured Cell of *Lagerstroemia speciosa*

Figure 6:
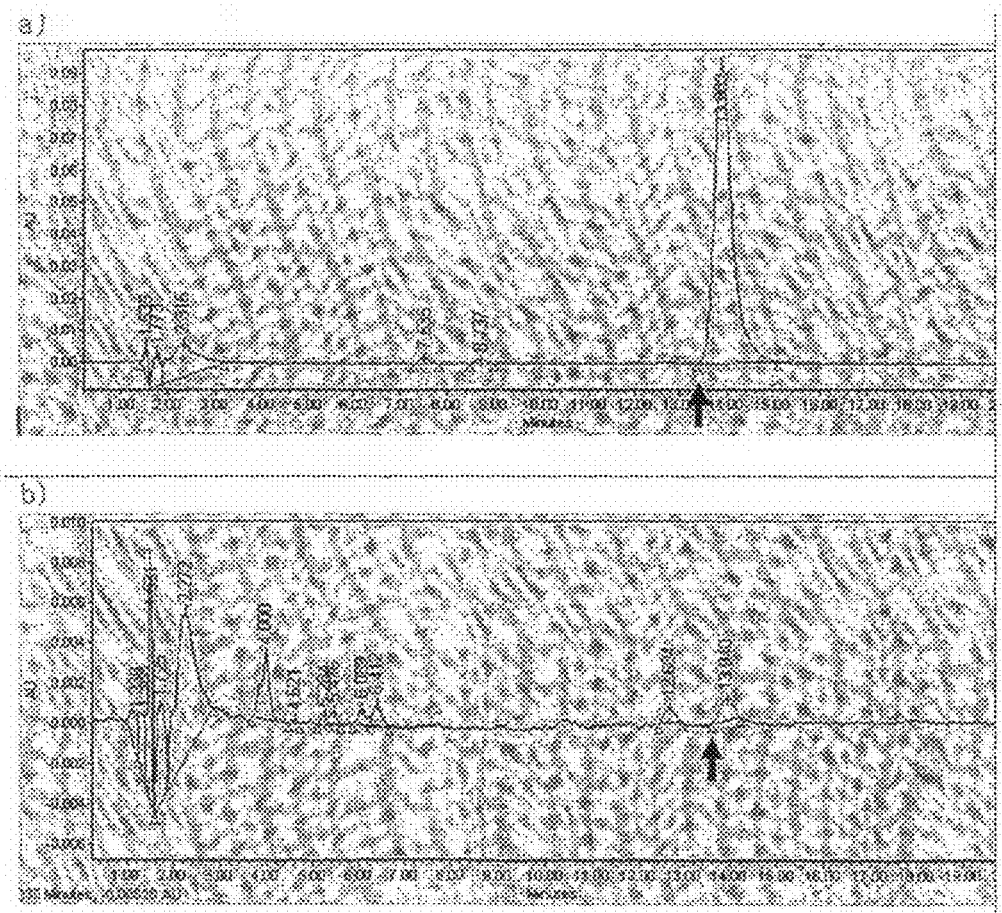
FIG. 6 shows the analysis result of High Performance Liquid Chromatography for corosolic acid in methanol extract of the suspension-cultured cells of Banaba as illustrated in Example 6-3. [(a) corosolic acid standard sample at a concentration of 1 mg/ml, (b) methanol extract of the suspension-cultured cells of Banaba]

According to the method of EXAMPLE 6-2, *Lagerstroemia speciosa* cells were cultured, and then collected after 14 days. Then the productivity of corosolic acid was measured according to the method of EXAMPLE 2-3. The productivity of corosolic acid produced by culturing *Lagerstroemia speciosa* in mB5 medium is shown in Table 11. In addition, corosolic acid contained in the methanol extract of the suspension-cultured cell of *Lagerstroemia speciosa* was analyzed according to the method of Example 2-2,and the result shown in FIG. 6 (in FIG. 6, a: 1 mg/ml of corosolic acid standard, and b: the Methanol extract of the suspension-cultured cells of *Lagerstroemia speciosa*)

TABLE 11

| | Productivity of corosolic acid | |
|---|---|---|
| Cell line | (% DW) | (mg/L) |
| SYG-3 | 0.56 | 36.4 |

As shown in Table 11,the suspension-cultured cell of *Lagerstroemia speciosa* in mB5 medium produced 0.56% DW of corosollc acid. This result was 56 times higher than the 0.01% of corosollc acid contained in a leaf of *Lagerstromia speciosa* (Chem Pharm. Bull. 41 12:2129-2131, 1993).

The present invention relates to a method of mass production for corosolic acid by using the cell suspension culture method, thereby producing an increased level of 25 times to 56 times as that in the natural leaf. The present invention can maximize the volumetric productivity which is an important factor in commercialization of the plant cell suspension culture, greatly contributing to the production of source material used for health foods and medication.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. A method of producing corosolic acid by using plant cell suspension culture comprising the steps of:
    (a) inducing a callus from a tissue of plant producing corosolic acid;
    (b) preparing a suspension-cultured cell line capable of being cultured in liquid culture medium from the induced callus;
    (c) culturing the prepared suspension-cultured cell line in a suspension culture;
    (c-1) culturing by transferring the cell line to a medium containing an elicitor: and
    (d) isolating corosolic acid from the culture solution obtained in the suspension culture step (c-1), wherein the elicitor is selected from the group consisting of biological elicitors and non-biological elicitors.

2. The method of claim 1, wherein the plant producing corosolic acid is selected from the group consisting of *Eriobotrya japonica, Lagerstroemla speciosa, Temstroemia gymnanthera, Crataegus pinnatifida*, and *Tiarella polyphylla*.

3. The method of claim 1, wherein the suspension-cultured cell line is a cell line of *Eriobotrya japonica* Lindl. SYG-2 (accession no. KCTC 10822BP), or a cell line of *Lagerstromia speciosa* SYG-3 (accession no. KCTC 10823BP).

4. The method of claim 1, wherein in step (a), the callus is induced by culturing the plant tissue on Linsmaler & Skoog medium, or Murashige & Skoog medium.

5. The method of claim 1, wherein the medium further comprises one or more selected from the group consisting of α-naphtalene acetic acid and 6-benzylaminopurine.

6. The method of claim 1, wherein in step (c), the cell line is in Linsmaler & Skoog medium, or Gamborg's B5 medium.

7. The method of claim 1, wherein the medium of step (c-1) is Gamborg's B5 medium or modified Gamborg's B5 medium.

8. The method of claim 1, wherein the elicitor is treated one or more times.

9. The method of claim 1, wherein the non-biological elicitor is selected from the group consisting of silver nitrate, sodium butyrate, and methyl jasmonate.

10. The method of claim 9, wherein silver nitrate is treated at a concentration of 0.01 to 500 μM.

11. The method of claim 9, wherein sodium butyrate is treated at a concentration of 0.01 to 500 mM.

12. The method of claim 9, wherein methyl jasmonate is treated at a concentration of 0.1 μM to 50 mM.

13. The method of claim 1 wherein the biological elicitor is selected from the group consisting of an extract of fungi, and extract of bacteria, and extract of yeast, chitosan, lichenan, glucomannan, pleuran, glucan, carboxylmethylglucan, sulfoethylglucan, hydroxymethylglucan, mannan, xylan, mannobiose, mannotriose, mannopentaose, mannotetraose, cellulysin, Multifect XL, Multifect CL, resinase, pilpxyme, SP 431, pectinal, rapidase, and chitinase.

14. The method of claim 1 wherein the initial concentration of inoculated cells is 1 to 20 g/L DW (cell dry weight).

15. The method of claim 1 wherein the medium comprises a carbon source in an amount of 1 to 20%(w/v).

16. A method of suspension culture of *Eriobotrya japonica* or *Lagerstromia speciosa* comprising the steps of:
  (a) inducing a callus from *Eribotrya japonica* or *Lagerstromia speciosa*;
  (b) preparing a cell line capable of being cultured in liquid culture medium from the induced callus;
  (c) culturing the cell line in a suspension culture; and
  (d) culturing by transferring the cell line to a medium containing an elicitor.

17. The method of claim 16, wherein the cell line is a cell line of *Eriobotrya japonica* Lindl. SYG-2 (accession no. KCTC 10822BP), or a cell line of *Lagerstromia speciosa* SYG-3 (accession no. KCTC 10823BP).

* * * * *